United States Patent [19]  [11] 4,009,268
Cardon et al.  [45] Feb. 22, 1977

[54] COMPOSITION AND METHOD FOR REDUCING THE INCIDENCE OF SCOURS IN NEO-NATAL RUMINANTS

[75] Inventors: Bartley P. Cardon; Howard M. Frederick, both of Tucson, Ariz.

[73] Assignee: Arizona Feeds, Tucson, Ariz.

[22] Filed: Oct. 6, 1975

[21] Appl. No.: 619,904

Related U.S. Application Data

[63] Continuation-in-part of Ser. No. 326,629, Jan. 26, 1973, Pat. No. 3,911,114.

[52] U.S. Cl. .................................. 424/180; 424/127
[51] Int. Cl.$^2$ ................ A61K 31/715; A61K 33/00
[58] Field of Search ........................... 424/180, 127

[56] References Cited

UNITED STATES PATENTS 3,911,114  10/1975  Cardon .............................. 424/180

OTHER PUBLICATIONS

Welsby–Chem. Abst. vol. 72 (1970) p. 53889q.

*Primary Examiner*—Sam Rosen
*Attorney, Agent, or Firm*—Wills, Green & Mueth

[57] ABSTRACT

Neo-natal ruminants are fed an aqueous mixture containing pregelatinized starch for at least the first several feedings after the feeding of colostrum milk is stopped.

12 Claims, No Drawings

COMPOSITION AND METHOD FOR REDUCING THE INCIDENCE OF SCOURS IN NEO-NATAL RUMINANTS

CROSS-REFERENCE TO RELATED APPLICATION

This application is a continuation-in-part of application Ser. No. 326,629, now patent No. 3,911,114.

BACKGROUND AND SUMMARY OF THE INVENTION

By far, the main cause of death of neo-natal calves in the dairy industry, is "scours" or "diarrhea".

It is estimated that twelve million dairy calves (as differentiated from beef calves) are born each year, and that 50% of these neo-natal calves usually develop scours shortly after being taken away from the cow, i.e. after the intake of colostrum or "first milk" is stopped.

Of the calves which develope scours, 40% usually die, and the other 60% which recover, are usually weak and "off" feed, thereby losing as much as one or two months of growth.

Thus, it will be readily apparent that the frequent occurrence of scours in neo-natal dairy calves is a source of considerable expense and trouble to those in the dairy industry.

Accordingly, it is an object of the present invention to provide a novel composition and method for reducing the incidence of scours in neo-natal ruminants, which is highly effective from the standpoint of almost completely preventing the occurrence of scours in neo-natal dairy calves.

Another object of the present invention is to provide such a composition and method which is relatively inexpensive and easy to use.

A further object of the present invention is to provide a feed supplement which can be used for the first few days of the feeding of the neo-natal ruminant after the feeding of colostrum milk is stopped, and which includes the preventative composition as well as vitamins and minerals which are physiologically beneficial to the animal.

Yet another object is to provide a milk replacer product which is the sole food source for the neo-natal calf for the first 30 days of feeding and which also includes the aforementioned preventative composition.

We have discovered that the aforementioned objects and advantages are achieved by feeding to neo-natal ruminants, as the first feedings after the intake of colostrum or first milk is stopped, an aqueous mixture containing in the neighborhood of 30 grams of pregelatinized starch, preferably with additional amounts of vitamins and minerals which are physiologically beneficial to the animal.

DETAILED DESCRIPTION

For simplicity of explanation, the present invention is described as used with neo-natal dairy calves, but the invention is equally applicable for use with other newborn ruminant animals.

As is well known to those familiar with the dairy industry, a newborn dairy calf is usually left with the cow for about 12 hours for the feeding of colostrum milk, often referred to as "first milk", which milk contains antibodies helpful for the protection of the newborn animal against sickness and diseases, including the aforementioned scours.

After about 12 hours, the calf is usually taken from the cow and the latter returned to the herd. In some instances, as where the cow refuses to accept the calf, the latter is fed first milk from the "pooled" first milk from other cows.

As mentioned above, after the day old calf is taken away from the cow, approximately 50% of these animals develope diarrhea or scours. This causes the animal to lose large quantities of body fluid, and usually in the neighborhood of 40% of those so afflicted, will die. The other 60% eventually recover without treatment, but because of their weakened condition, they are "off" feed, and lose approximately one or two months of growth time.

We have discovered that the incidence of scours in such neo-natal dairy calves can be greatly reduced, and in many instances substantially eliminated, by feeding to the animal an aqueous mixture containing about 30 grams of pregelatinized corn starch in a quart of liquid food, for example, whole milk or a so-called milk replacer product.

The pegelatinized starch which we have used with considerable success was obtained from The Hubinger Company, Keokuk, Iowa, and sold by it under the designation "OK PRE-GEL". This is a pure, highly refined corn starch which is pregelatinized in water, dehydrated and pulverized to a white, finely granulated solid having a uniform particle size and a moisture content of about 3.5% to about 8.0%. The water absorption capacity of this pregelatinized starch is greater than 15 to 1.

The aqueous mixture is fed to the calf for at least its first two feedings (during one day), following its removal from being fed colostrum or first milk. For these first feedings of the mixture, a nipple and bottle (or the equivalent of a bottle) arrangement is normally used.

We have also discovered that it is beneficial to the health of the animal and for substantially eliminating the incidence of scours, to feed to the calf for the first two days (i.e. a total of four feedings) after being taken off of colostrum milk, a complete food supplement comprising an aqueous mixture containing both the aforementioned ration of pregelatinized starch as well as various vitamins and minerals and protein and energy sources which are physiologically beneficial to the ruminant animal.

The composition of such a dry food supplement, sold by Arizona Feeds, Tucson, Arizona, under the trademark "Calf Booster", and which is intended to be mixed with a liquid carrier to provide 2 ounces of dry composition per quart of aqueous mixture, preferably contains the following components on a dry weight percentage basis.

| Component | Dry Weight Percentage |
| --- | --- |
| pregelatinized starch | 55.00 |
| cerelose | 12.00 |
| dried milk product | 20.00 |
| dried egg | 5.75 |
| sodium phosphate | 2.00 |
| salt | 1.00 |
| calcium lactate | 1.00 |
| potassium chloride | 1.00 |
| vitamin premix | 2.00 |
| chelated trace minerals (ruminant) | 0.25 |
| | 100.00 |

The preferred chelated trace minerals are described in U.S. Pat. No. 2,960,406, and can be obtained from Arizona Feeds, Tucson, Arizona, under the designation "CTM Chelated Trace Minerals (Ruminant)".

The vitamin pre-mix comprises a mixture of vitamins and minerals which are dietically important to the health of the ruminant. Such a vitamin pre-mix can be obtained from Hoffman-Taff Inc., under the designation Ruminant Vitamin Pre-mix, and preferably includes vitamin A palmitate, D-activated animal sterol (source of Vitamin D), alpha tocopheryl acetate, riboflavin supplement, niacin, d-pentothenic acid, vitamin B12 supplement, and choline chloride (B complex vitamin).

The results of two typical trials of day-old Holstein bull and heifer calves, using control calves, calves fed an aqueous mixture containing pegelatinized starch, and calves fed an aqueous mixture containing Arizona Feed "Calf Booster" food supplement, are tabulated below.

With the control calves, each had two feedings of colostrum milk or first milk the first day, followed by routine feedings of non-colostral milk for the duration of the trial.

For the calves fed an aqueous mixture containing pregelatinized starch, each had two feedings of colostrum milk the first day, as with the control calves, and thereafter, 30 grams of pregelatinized starch was mixed into the first four feedings of non-colostral milk during the second and third days.

For the calves fed "Calf Booster" supplement, each calf received two feedings of colostrum milk during the first day, as with the control calves, and thereafter, two ounces of "Calf Booster" supplement was mixed into the first four feedings of non-colostral milk during the second and third days.

The calves were fed at 5:00 a.m. and 3:30 p.m. each day.

When scours were observed in the control calves, four ounces of Arizona Feed "Calf Booster" supplement was added to the non-colostral milk at each feeding until the diarrhea was stopped.

When calves being fed pregelatinized starch or "Calf Booster" supplement scoured, they were continued on their routine test diet until the prescribed period was ended, at which time they received 4 ounces of Arizona Feed "Calf Booster" supplement at each feeding, in the same manner as with the control calves which had scoured.

EXAMPLE I

Thirty grams of Pregelatinized Starch

EXAMPLE I

Thirty (30) grams of Pregelatinized Starch

| | Control | Treatment |
|---|---|---|
| Number of calves | 4 | 4 |
| Number with diarrhea | 4 | 1 |
| Time to onset of diarrhea, hours[1] | 24 | 84 |
| Severity of diarrhea[2] | 3.8 | 2.0 |
| Number of scoured calves treated for diarrhea[3] | 4 | 1 |
| Number of calves responding to treatment | 4 | 1 |
| Duration of diarrhea | 78 | 48 |

[1]From the time calves were received to the first sign of diarrhea.
[2]0 = firm, 1 = pasty firm, 2 = pasty, 3 = pasty watery, 4 = watery.
[3]Once diarrhea was confirmed, 4 ounces of Calf Booster supplement was administered at each feeding until diarrhea was stopped.

EXAMPLE II

Two Ounces of "Calf Booster" Supplement (Containing 30.8 grams of pregelatinized starch)

EXAMPLE II

Two Ounces of "Calf Booster" Supplement (Containing 30.8 grams of pregelatinized starch)

| | Control | Treatment |
|---|---|---|
| Number of calves | 5 | 5 |
| Number with diarrhea | 5 | 2 |
| Time to onset of diarrhea, hours[1] | 43.2 | 140.0 |
| Severity of diarrhea[2] | 2.1 | 0.4 |
| Number of scoured calves treated for diarrhea[3] | 5 | 2 |
| Number of calves responding to treatment | 5 | 2 |
| Duration of diarrhea | 52.4 | 18.0 |

[1]From the time calves were received to the first sign of diarrhea.
[2]0 = firm, 1 = pasty firm, 2 = pasty, 3 = pasty watery, 4 = watery.
[3]Once diarrhea was confirmed, 4 ounces of Calf Booster was administered at each feeding until diarrhea was stopped.

Although we do not intend to be held to any theory as to how and why the feeding to neo-natal calves of an aqueous mixture containing pregelatinized starch appreciably reduces the incidence of scours, it appears that the starch gel forms a coating or lining on the intestines of the animal, thereby slowing down the movement of products through the intestine, reducing the flow of body fluids into the intesine, and deterring micro-organisms in the intestines from damaging or adversely affecting the wall of the intestine, as might occur if the endotoxins produced by the micro-organisms were permitted to contact the intesting wall.

We have also discovered a special milk replacer formulation containing pregelatinized starch, which supplies the daily nutritional requirements and which provides a continuing deterent to the incidence of scours in young dairy calves. This composition contains the following percentages of components, on a dry weight basis:

| Component | Dry Weight Percent |
|---|---|
| dried skim milk | 55.00 |
| dried whey product | 10.95 |
| cerelose | 15.00 |
| homogenized animal fat | 10.00 |
| pregelatinized starch | 7.00 |
| salt | 1.00 |
| vitamin pre-mix | 1.00 |
| chelated trace minerals (ruminant) | 0.5 |
| | 100.00 |

The preferred chelated trace minerals and the vitamin pre-mix are the same as previously described.

The aforementioned trials utilizing pregelatinized starch and Arizona Feed "Calf Booster" supplement in the feeding of neo-natal dairy calves, showed a substantial decrease in the incidence of scours and a significant increase in the time to onset of scours or diarrhea.

Also, the severity of diarrhea, measured either at the peak of scours or the average stool composition from onset of diarrhea to the control thereof, was greatly reduced when either composition was used.

The use of two ounces of "Calf Booster" supplement for each feeding was selected on the basis that it contained approximately 30 grams of pregelatinized starch, to compare the results of the use of pregelatinized starch both with and without additional vitamins and minerals.

Comparing the results of the two trials, it appears that the use of "Calf Booster" supplement, with its combination of pregelatinized starch and nutrients, is more effective than pegelatinized starch alone for increasing the time to onset of scours, for reducing the severity of diarrhea, and for decreasing the recovery time of subsequent treatment for diarrhea.

We claim:

1. The method of reducing the incidence of sours in neo-natal ruminant animals, comprising feeding to the animal an aqueous mixture containing an effective amount of pregelatinized starch.

2. The method according to claim 1 in which the amount of pregelatinized starch per feeding is about thirty (30) grams.

3. The method according to claim 1 in which the pregelatinized starch is corn starch.

4. The method according to claim 1 in which the animal is started on colostrum milk, and the pregelatinized starch is mixed with the liquid for the first feeding following the stopping of the feeding of colostrum milk to the animal.

5. The method according to claim 4 in which the animal is fed colostrum milk for the first day.

6. The method according to claim 4 in which the animal receives at least two feedings containing pregelatinized starch, following the feedings on colostrum milk.

7. The method according to claim 4 in which the pregelatinized starch is mixed with non-colostral milk.

8. The method according to claim 2 in which the mixture contains minor amounts of vitamins and minerals which are physiologically beneficial to the animal.

9. The method of reducing the incidence of scours in neo-natal ruminants which are started on feedings of colostrum milk and such feedings then stopped, which includes the step of depositing on the wall of the intestines of the animal after such stoppage, an effective amount of a starch gel.

10. The method according to claim 9 in which the gel is a corn starch gel.

11. The method of claim 9 in which the gel also contains vitamins and minerals which are physiologically beneficial to the animal.

12. The method according to claim 9 in which the gel also contains chelated trace minerals.

* * * * *

UNITED STATES PATENT AND TRADEMARK OFFICE
Certificate

Patent No. 4,009,268            Patented February 22, 1977

Bartley P. Cardon and Howard M. Frederick

Application having been made by Bartley P. Cardon and Howard M. Frederick, the inventors named in the patent above identified, and Arizona Feeds, Tucson, Arizona, a corporation of Arizona, the assignee for the issuance of a certificate under the provisions of Title 35, Section 256, of the United States Code, deleting the name of Howard M. Frederick as a joint inventor, and a showing and proof of facts satisfying the requirements of the said section having been submitted, it is this 27th day of June 1978, certified that the name of the said Howard M. Frederick is hereby deleted from the said patent as a joint inventor with the said Bartley P. Cardon.

FRED W. SHERLING,
*Associate Solicitor.*